(12) United States Patent
O'Mongain

(10) Patent No.: US 7,027,149 B2
(45) Date of Patent: Apr. 11, 2006

(54) PHOTOMETRIC ANALYSIS OF NATURAL WATERS

(75) Inventor: Eon O'Mongain, Dublin (IE)

(73) Assignee: Jeacle Limited, Dublin (IE)

( * ) Notice: Subject to any disclaimer, the term of this patent is extended or adjusted under 35 U.S.C. 154(b) by 0 days.

(21) Appl. No.: 10/275,954

(22) PCT Filed: May 16, 2001

(86) PCT No.: PCT/IE01/00067

§ 371 (c)(1),
(2), (4) Date: Dec. 17, 2002

(87) PCT Pub. No.: WO01/88505

PCT Pub. Date: Nov. 22, 2001

(65) Prior Publication Data

US 2004/0130713 A1    Jul. 8, 2004

(30) Foreign Application Priority Data

May 16, 2000    (IE)    .............................. S2000/0376

(51) Int. Cl.
*G01J 3/00*    (2006.01)
(52) U.S. Cl. ...................................... 356/300; 356/445
(58) Field of Classification Search ................ 356/300, 356/445; 250/339.07, 339.12; 702/27
See application file for complete search history.

(56) References Cited

U.S. PATENT DOCUMENTS

| 2,866,899 A | * | 12/1958 | Busignies et al. | .......... 356/326 |
|---|---|---|---|---|
| 3,603,952 A | * | 9/1971 | Smith | .......................... 356/445 |
| 5,242,602 A | * | 9/1993 | Richardson et al. | ........ 356/300 |
| 5,296,711 A | * | 3/1994 | Leonard et al. | ............. 250/301 |
| 5,304,492 A | * | 4/1994 | Klinkhammer | ............. 356/417 |
| 5,350,922 A | * | 9/1994 | Bartz | ......................... 356/338 |
| 5,384,589 A | * | 1/1995 | Ulich et al. | ..................... 348/31 |
| 5,446,681 A | * | 8/1995 | Gethner et al. | ................ 702/27 |
| 5,606,164 A | * | 2/1997 | Price et al. | ............. 250/339.09 |
| 6,028,663 A | * | 2/2000 | O'Mongain et al. | ......... 356/213 |
| 6,115,673 A | * | 9/2000 | Malin et al. | ................... 702/23 |
| 6,219,132 B1 | * | 4/2001 | Scharlack et al. | .......... 356/326 |
| 6,304,664 B1 | * | 10/2001 | Silva et al. | ................. 382/100 |
| 6,366,681 B1 | * | 4/2002 | Hutchins | ..................... 382/110 |

FOREIGN PATENT DOCUMENTS

EP    0915338 A2    5/1999

OTHER PUBLICATIONS

O'Mongain et al., "Spectral absorption coefficient measured in situ in the North Sea with a marine radiometric spectrometer system", Jul. 20, 1997, Applied Optics, vol. 36, No. 21, pp. 5162-5167.*

(Continued)

*Primary Examiner*—Hwa (Andrew) Lee
*Assistant Examiner*—Kara Geisel
(74) *Attorney, Agent, or Firm*—Jacobson Holman PLLC

(57) ABSTRACT

A spectrographic analysis method which is photometric and non-contact for determining the presence of a chosen constituent in water is provided based on the fact that the inverse of reflectance is a measure of absorption. A full spectrum measurement of the reflectance of the water is made and an absorption spectrum calculated which is then fitted to a clear spectrum in a wavelength range where the water absorption dominates so as to have scaling and offset. Then the clear water spectrum is subtracted and a matching is repeated for the spectrum of the desired constituent and thus a measure of the concentration of the constituent in the water is obtained.

19 Claims, 15 Drawing Sheets

OTHER PUBLICATIONS

Kutser et al, SPIE, vol. 2319, 1994, pp. 85-91, A remote sensing reflectance model of optically-active components . . . .

Corsini et al, IEEE 1999, pp. 943-945, Retrieval of the Conmcentration of Optically Active Constituents in the . . . .

Melack et al, IEEE 1994, pp. 2363-2365, Comparison of Spectral Feature Algorithms for Remote Sensing of Chlorophyll in . . . .

* cited by examiner

PHOTOMETRIC ANALYSIS OF NATURAL WATERS

This is a nationalization of PCT/IE01/00067 filed May 16, 2001 and published in English.

The present invention relates to a photometric analysis method for algae and other suspensions in water. In particular, the analysis is spectrographic analysis, which involves the measurement of spectral heights of the absorbance of a sample at predetermined wavelengths to obtain an estimate of the content of the suspensions.

The chlorophyll content in rivers, lakes, estuaries and the ocean is an important parameter in assessment of water quality. The chlorophyll concentration is an indicator of the growth of algae, which in turn is an indication of the presence of nutrients and other conditions such as solar energy for algae growth. This growth consumes available oxygen in the water. Thus, environmental scientists on the basis of chlorophyll concentration often quote a body's water trophic status. Thus, for example, water having a chlorophyll concentration of less than 2.5 µg/l would be considered ultra-oligotrophic, while a chlorophyll concentration greater than 75 µg/l would be considered hyper-trophic.

Suspended matter, including that due to algal growth and other constituents, such as sediments and effluents, also affects the properties and quality of a water body. Their presence limits light penetration and changes photosynthetic activity.

The monitoring of suspended solids is important in the water industry, particularly in the wastewater sector where the concentration of suspended matter released into natural waters is limited by water quality regulations. Similarly, in process water used within industries, suspended matter is often of critical importance to process efficiency or performance.

Dissolved organic matter (DOM) can also be present in water. This is matter that is not removed by filtering. It has a characteristic yellowing effect on water. Although not a danger to human health, it also restricts light transparency. In addition it tends to be a conservative quantity, and like salinity, can be used to indicate mixing rates between different waters in a bay or estuary.

Presently, the methods to determine algal concentrations are invasive methods, requiring taking water samples. A number of invasive methods are used to determine chlorophyll concentration.

Flourometry is one of the methods used for detecting chlorophyll presence in-vivo in real time i.e. without degradation of the sample. However, it can only be used to detect trends or changes in chlorophyll unless it is cross-calibrated by some other method for each specific algal suspension. Generally speaking it is not particularly satisfactory, though it is very useful for detecting trends in the tropic status of a particular body of water.

One of the problems with flourometry is that certain water contaminants, such as blue-green algae show hardly any flourescence when illuminated by blue or green light. Thus, in vivo fluorescent systems with blue and/or green illumination sources cannot give an effective estimate of chlorophyll content of blue-green algae. Considering that blue-green algae represents an important group of inland water algae, which are noted for their tendency to produce toxins, their detection is essential. It is therefore very important that any method of analysis of algae suspensions in water continues to be effective in the presence of the phycocyanin pigment unique to blue-green algae.

Another method of chlorophyll analysis is an extraction method (an in-vitro method) in combination with the use of some optical absorption method, or fluorescence, or high pressure liquid chromatography (HPLC). Generally with the optical absorption method sample colour pigments are concentrated in the extraction process and a spectral measurement of the chlorophyll absorption peak is used to quantify the chlorophyll concentration. For example, a sample of 500–1000 mls of contaminated water is first filtered which can take from an hour to two to overnight, depending on the volume of the sample. However, where vacuum assisted filtration can be applied, this greatly reduces filtration time. The filter paper containing the algae and suspended matter is then crushed and added to a quantity, usually 14 mls of methanol or ethanol, and boiled and centrifuged. Acetone extraction is another standard method often used without heating. At this stage the chlorophyll pigment is in solution in the methanol or ethanol so that the methanol or ethanol can be decanted into a cuvette, mounted into a spectrophotometer in which the absorbency of the extract is measured at two wavelengths. These two numbers are inserted into a particular algorithm to yield the "standard" measure of chlorophyll concentration.

While this method is not particularly costly, the need to have some form of extraction makes the analysis time consuming and involves the extra inconvenience and expense of handling methanol or ethanol. Also, the accuracy in determining the chlorophyll concentration depends on the quality of the extraction method. Thus, removing this step would eliminate the error introduced by this procedure.

Additionally, the extraction techniques due to the nature of chlorophyll use measurements of absorption at 665 and 750 nm. In methanol an absorption difference of the equivalent of $0.0072$ $m^{-1}$ in the unconcentrated sample is attributable to a chlorophyll concentration of 1 mg/m$^3$.

HPLC is a very efficient method of chlorophyll detection and indeed can distinguish between chlorophyll types and other pigments. However, it is an expensive system to purchase, operate and maintain and thus is not practical.

An additional method of chlorophyll analysis is described in EP915338 (O'Mongain), which uses photometric analysis of a water sample using a diffuser and spectrophotometer for determining algal concentrations of water samples. This method allows an estimation of absorption and back scatter, from which the absorption and back scatter of a clean water sample is then subtracted, allowing an exact method of determining chlorophyll concentration. However, this method still requires removing and analysing samples from water bodies.

Another method of measuring algal and suspended matter concentrations in water is to immerse optical instruments in water bodies and measure the optical properties of the water including turbidity, beam extinction, absorption and fluorescence effects. Presently the concentration of suspended matter in water is inferred from the turbidity measurement (an in-vivo method) or measured by filtering a sample of water and determining the mass of suspended matter on a dried filter (an in-vitro method). A problem with these systems is that in coastal waters, the instruments develop excessive coatings of algae in as short a time as one week, thereby losing calibration accuracy. Providing cleaning and calibration service for such systems is very expensive in time and effort.

There are problems with both the in vivo and in vitro methods presently used to determine algal concentrations of natural water systems. What is needed is an improved method of analysing suspensions (both algal and other matter) in water which is non-contact and therefore nonfouling and eliminates the need for water sampling, filtration, extraction and concentration of water samples to obtain specific measurements.

When measuring suspended matter by turbidity measurement it is usual to immerse optical instruments in water bodies and measure the optical properties of the water including the light scattering properties. Non chlorophyllous suspended matter does not in general fluoresce; therefore the use of flourometry is not relevant.

Turbidity measuring systems are calibrated by reference to the light scattering property of an agreed suspension, usually formazine. They are thus "substance based" in their calibration. Two different instruments may agree with each other when measuring formazine and disagree with each other when measuring another suspension. The light scattering characteristics of other substances may not be the same as formazine; colour, absorption, or scattering phase function can differ.

Presently the concentration of Dissolved Organic Matter (DOM) in water is determined by filtering a sample and measuring the absorption coefficient of the filtrate at one wavelength near 400 nm. One object of the present invention is to provide a non-invasive method to determine chlorophyll content of water suspensions.

Another object of the present invention is to determine the total suspended matter in water in physical units in a non-invasive manner. In summary, the invention is directed to providing better optical characterisation of suspended matter and other constituents.

A still further object of this invention is to obtain a non-invasive measure of DOM based on its absorption characteristics.

An additional object of this invention is to obtain a measure of other pigments, dyes and substances in a water suspension in a non-invasive manner, without the need to collect water samples.

STATEMENTS OF INVENTION

According to the invention, there is provided a spectrographic analysis method of determining the presence of a chosen constituent in water where such constituent gives rise to optically identifiable distinct characteristics comprising the steps, not necessarily sequentially, of:
 a full spectrum measurement of the reflectance of the body of water is prepared;
 the required optical characteristic is obtained from the full spectrum measurement;
 a wavelength range over which the chosen constituent optically identifiable distinct characteristic is dominant is chosen;
 the same optical characteristic over the wavelength range is determined as a datum spectrum for clear water; and
 the difference between the two spectra within the wavelength range is used to obtain a measure of the amount of the constituent present.

In one embodiment of the invention, where the required optical characteristic is present in the absorption spectrum and the method comprises:
 a full spectrum measurement of the reflectance of a body of water is prepared;
 an absorption spectrum of clear water is prepared as a datum spectrum;
 a potential absorption spectrum is derived from the reflectance measurement as a sample spectrum;
 the sample spectrum is matched to the datum spectrum at wavelength regions of the spectrum where the datum spectrum is the dominant contributor to spectral change to give a measure of the total absorption of the sample water;
 a known spectral signature of the chosen constituent is taken;
 the datum spectrum is removed from the sample spectrum to leave a residual spectrum for all the constituents in the water;
 a spectral signature for a prime chosen constituent is matched to the residual spectrum at a wavelength region where the chosen constituent is dominant; and
 the matched spectrum is abstracted as a measure of the amount of the prime chosen constituent in the water.

The wavelength regions chosen for matching with the datum spectrum are those closest to where the chosen constituent is dominant. The matched spectrum may be removed from the residual spectrum. In this latter method, a spectrum signature of another chosen constituent is matched to the new residual spectrum abstracted and removed as for the prime constituent.

In one method according to the invention, the constituents chosen are chlorophyll as the prime constituent, then DOM and the new residual spectrum, after the spectra for chlorophyll and DOM has been removed, is used as a measure of suspended matter and other constituents.

In one method according to the invention, additionally the spectrum attributable to surface reflection is identified and removed from the full spectrum measurement of the reflectance of the body of water prior to devising the potential absorption spectrum.

In one method, when in the chosen region, where the datum spectrum is dominant, there is also a spectrum relating to another constituent which could affect the estimate of the constituent being measured, the spectrum of this other constituent is first obtained and combined with the datum spectrum to provide a modified datum spectrum for removal from the sample spectrum.

One method according to the invention comprises steps in which:
 the total spectrum of reflectance is taken;
 a region of significant water absorption is chosen;
 the effect of the geometry of the illumination is determined and the backscattering is estimated.

The invention also provides apparatus for carrying out the method as claimed in any preceding claim comprising:
 means for collecting light reflected from a body of water;
 a spectrometer for preparing a reflectance spectrum of the reflected light; and
 a processor unit having processing means to carry out the steps of the method using the reflectance spectrum.

Further, the invention comprises a computer program comprising program instructions for causing a computer to carry out the steps of the method as described above.

Further, the invention comprises the method as described above or the processing means of the apparatus. Further, the computer program can be embodied in a record medium, stored in a computer memory, embodied on a read only memory or carried on an electrical signal carrier.

DETAILED DESCRIPTION OF THE INVENTION

The invention will be more clearly understood from the following description of some embodiments and methods thereof, given by way of example only, with reference to the accompanying drawings, in which.

Figure 7:
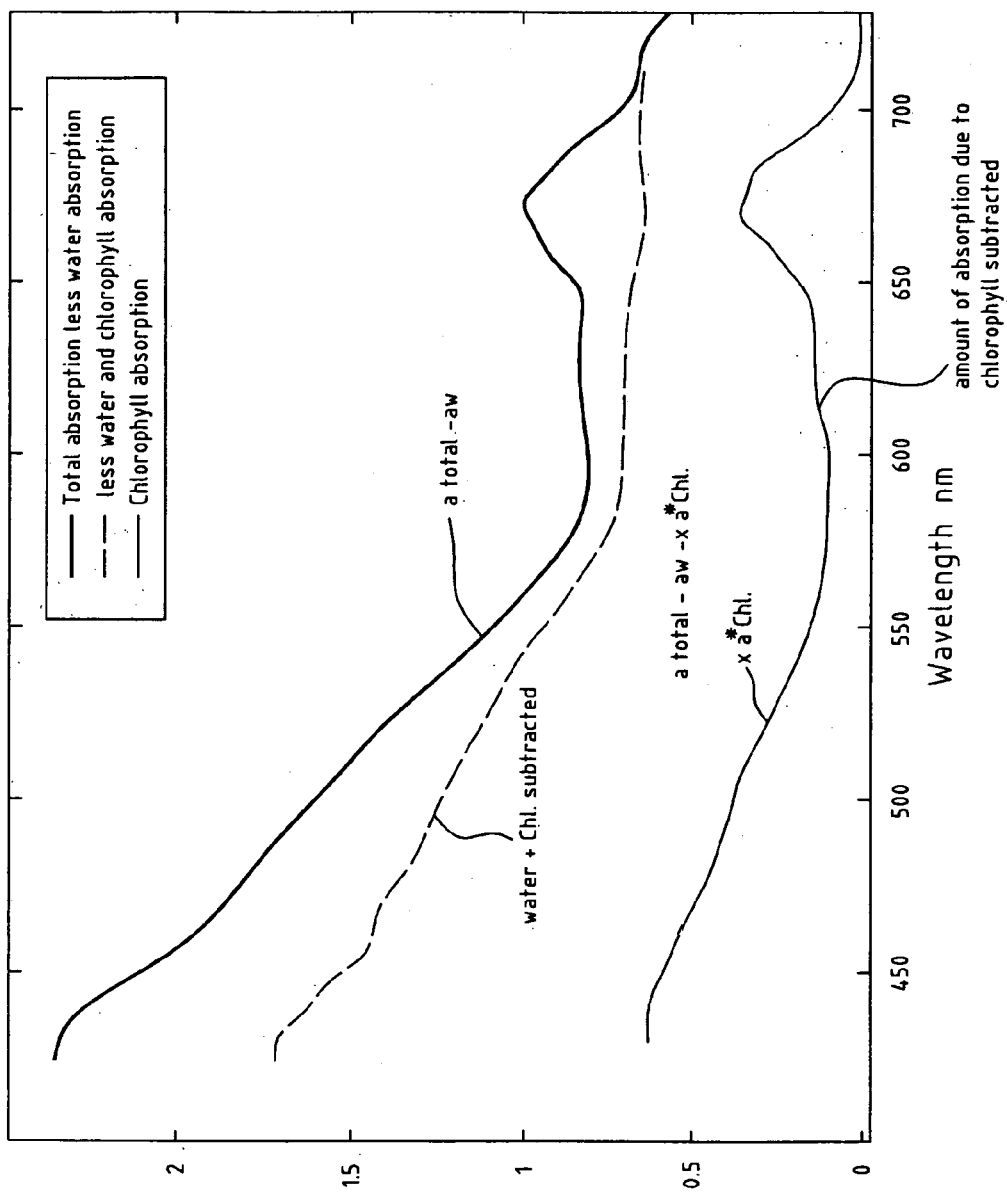
Figure 8:
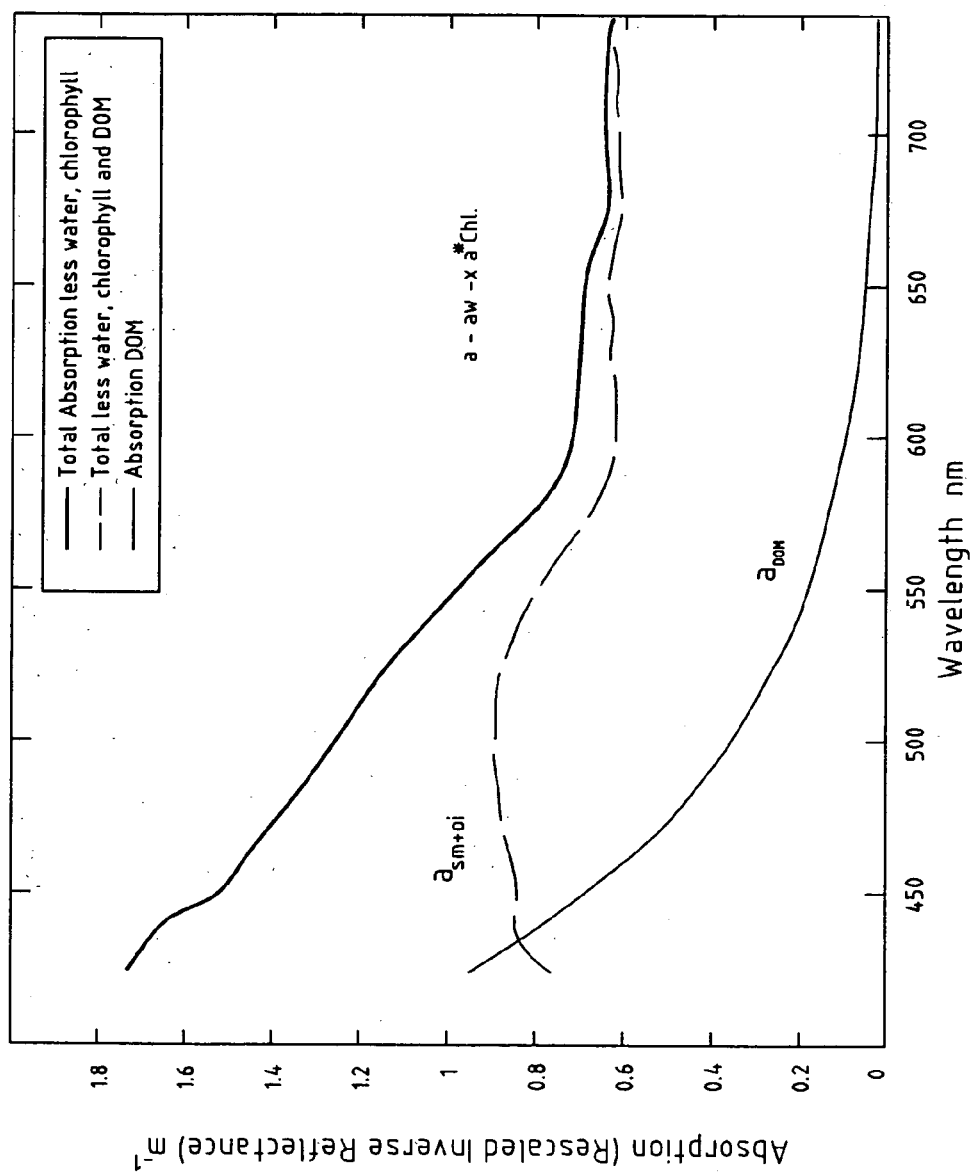
Figure 9:
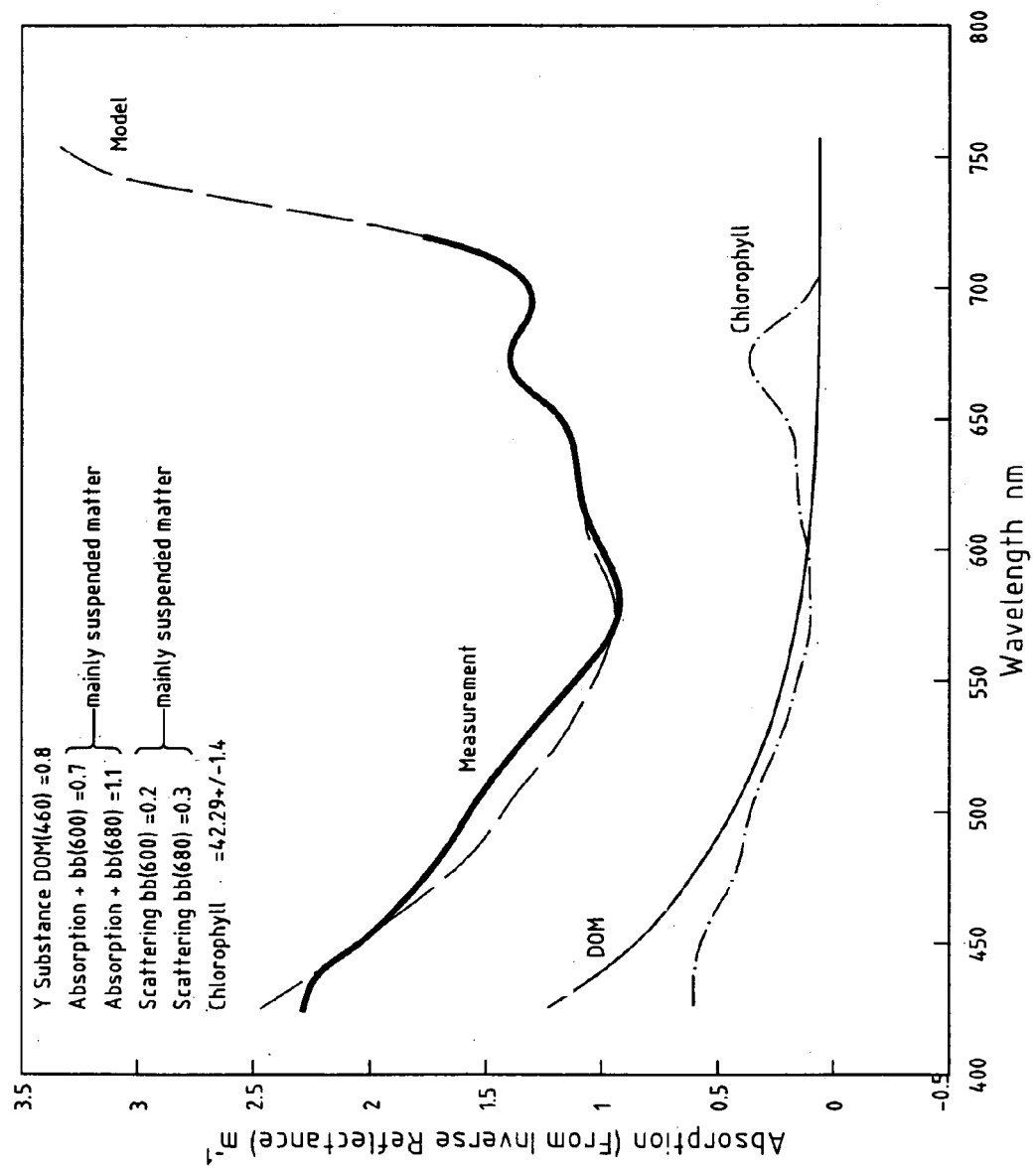
Figure 10:
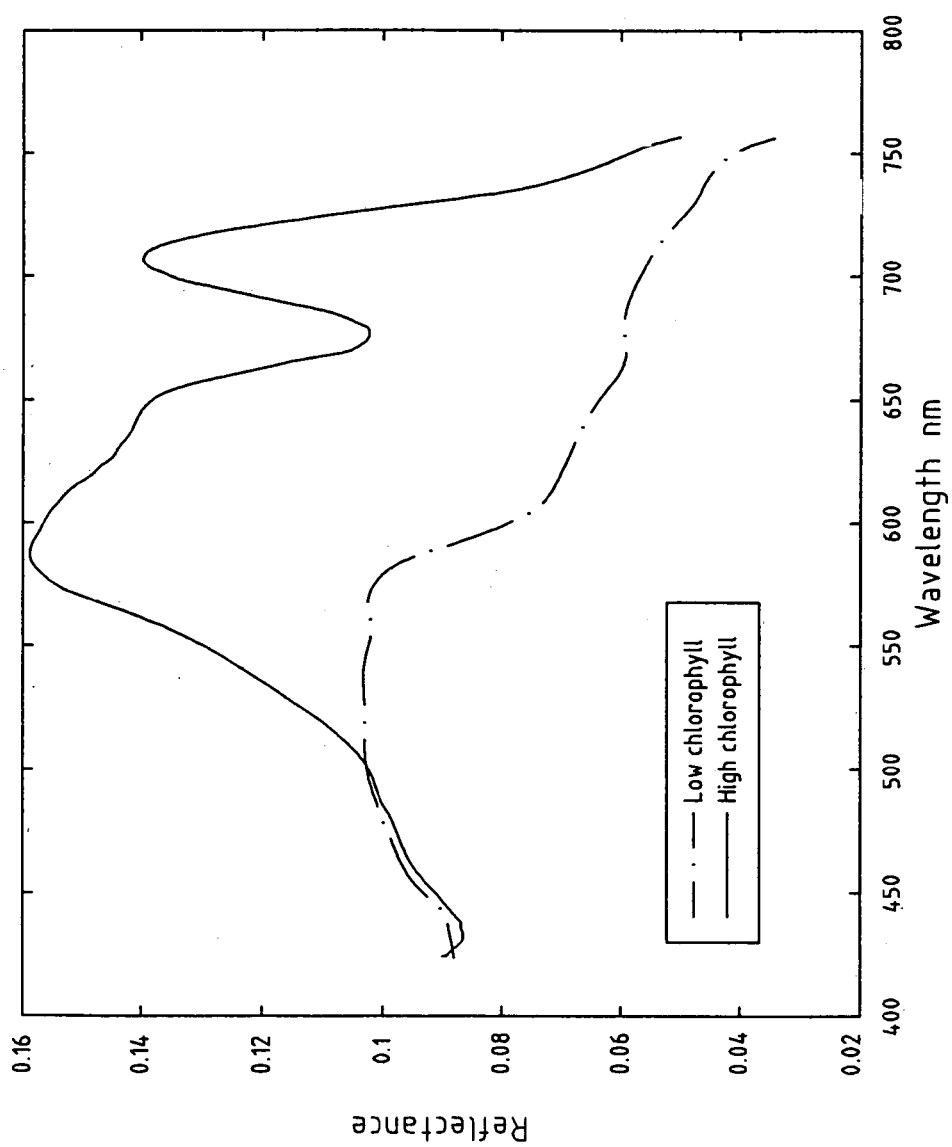
Figure 11:
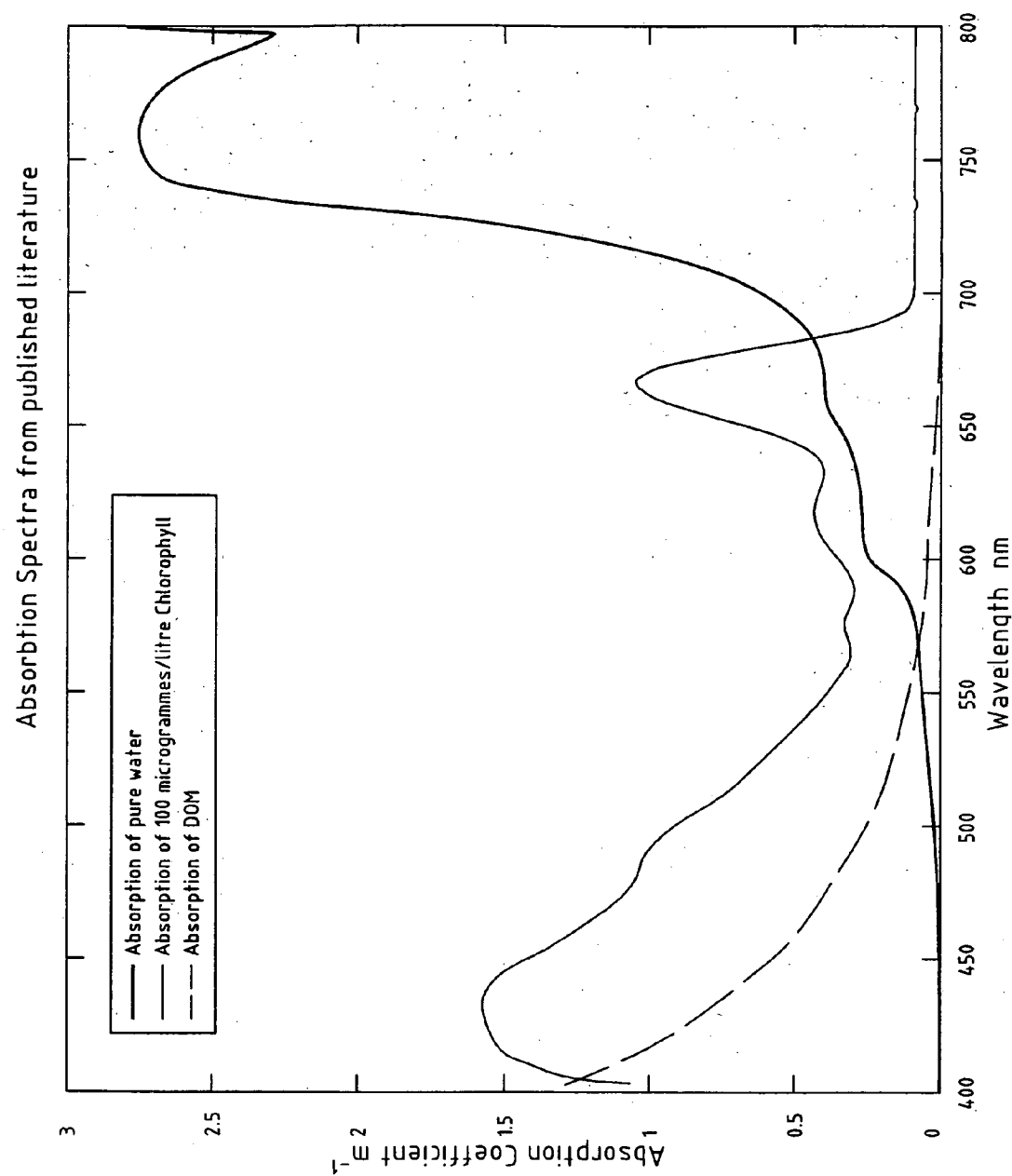
Figure 12:
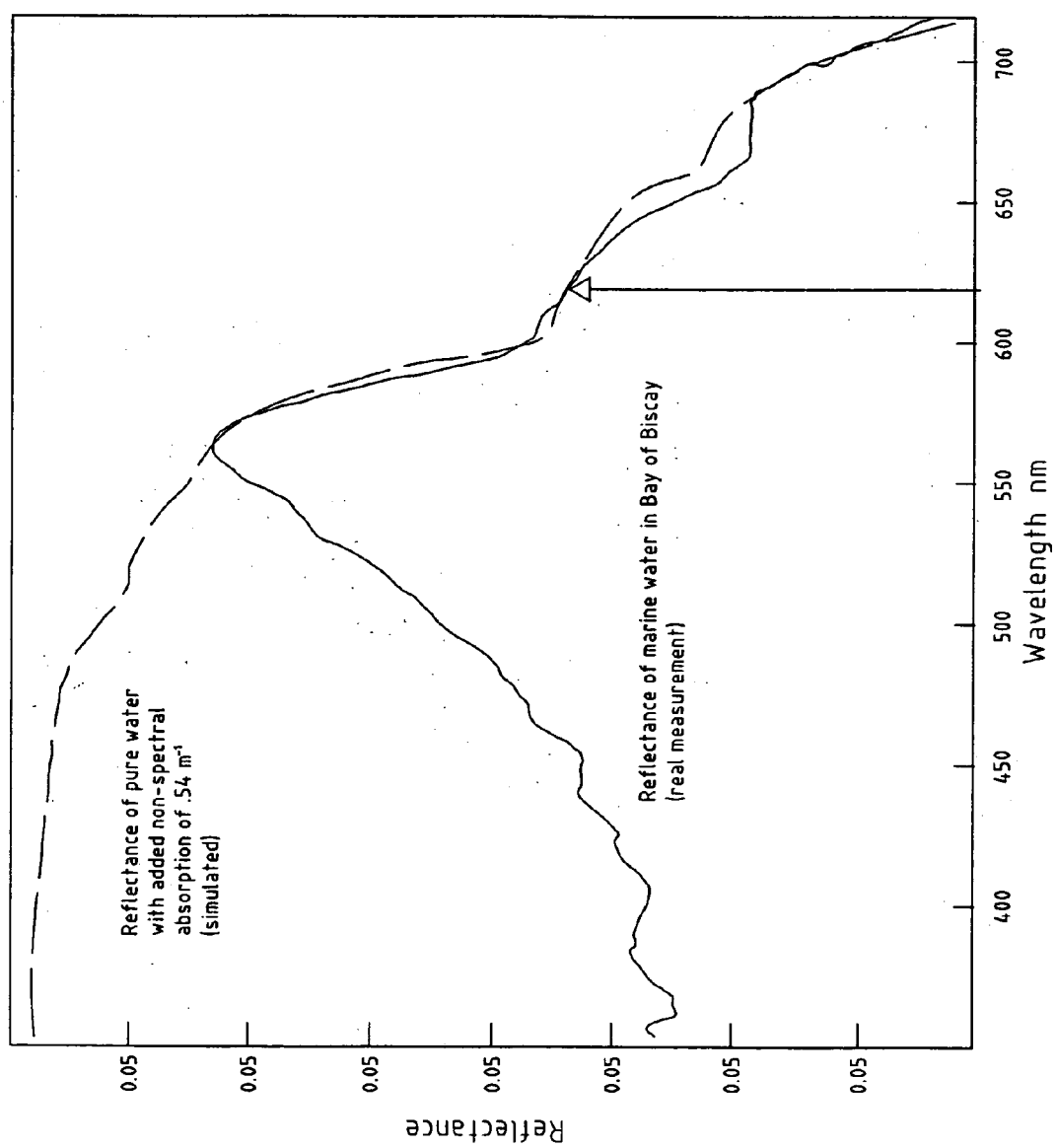
Figure 13:
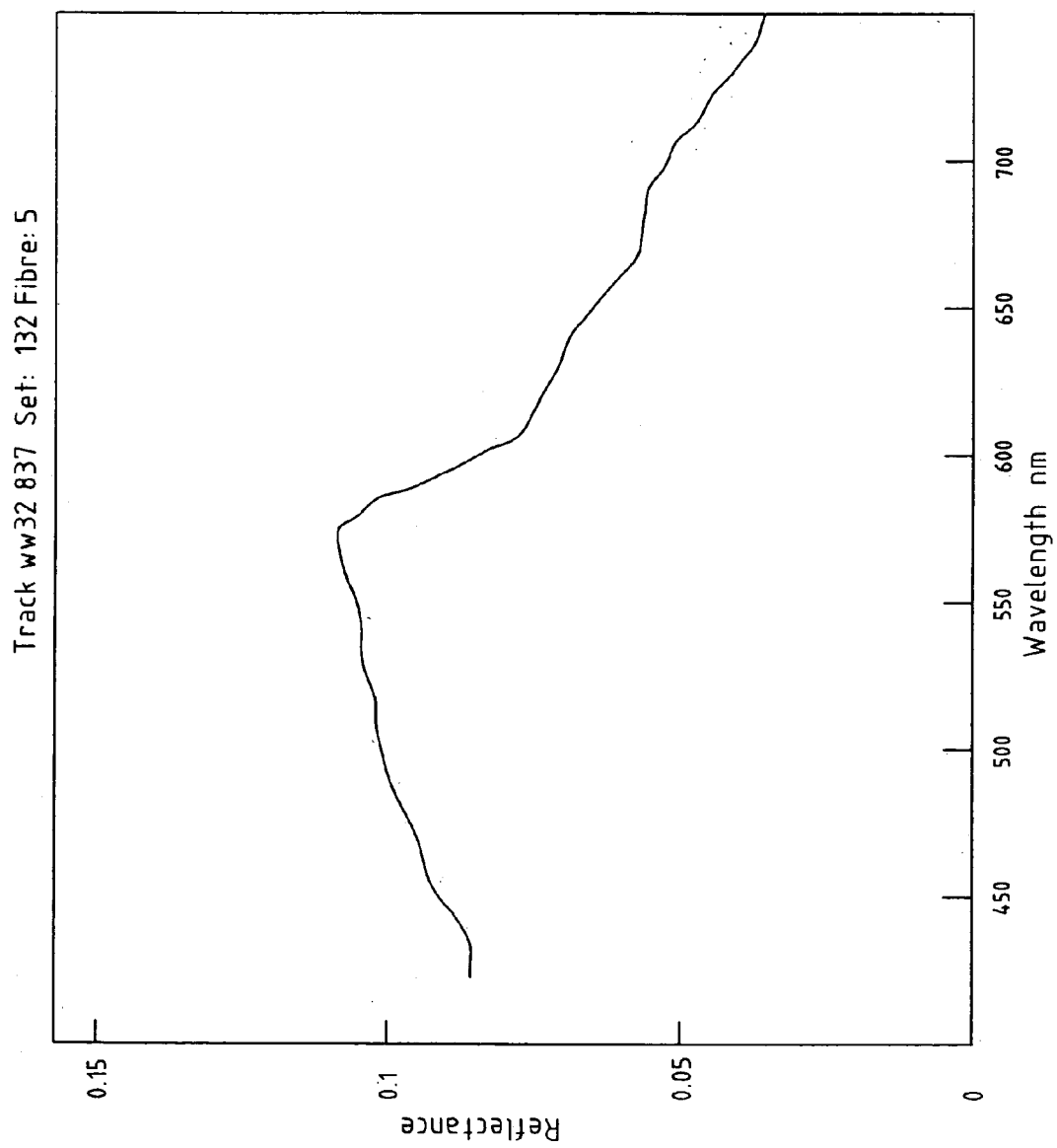
Figure 14:
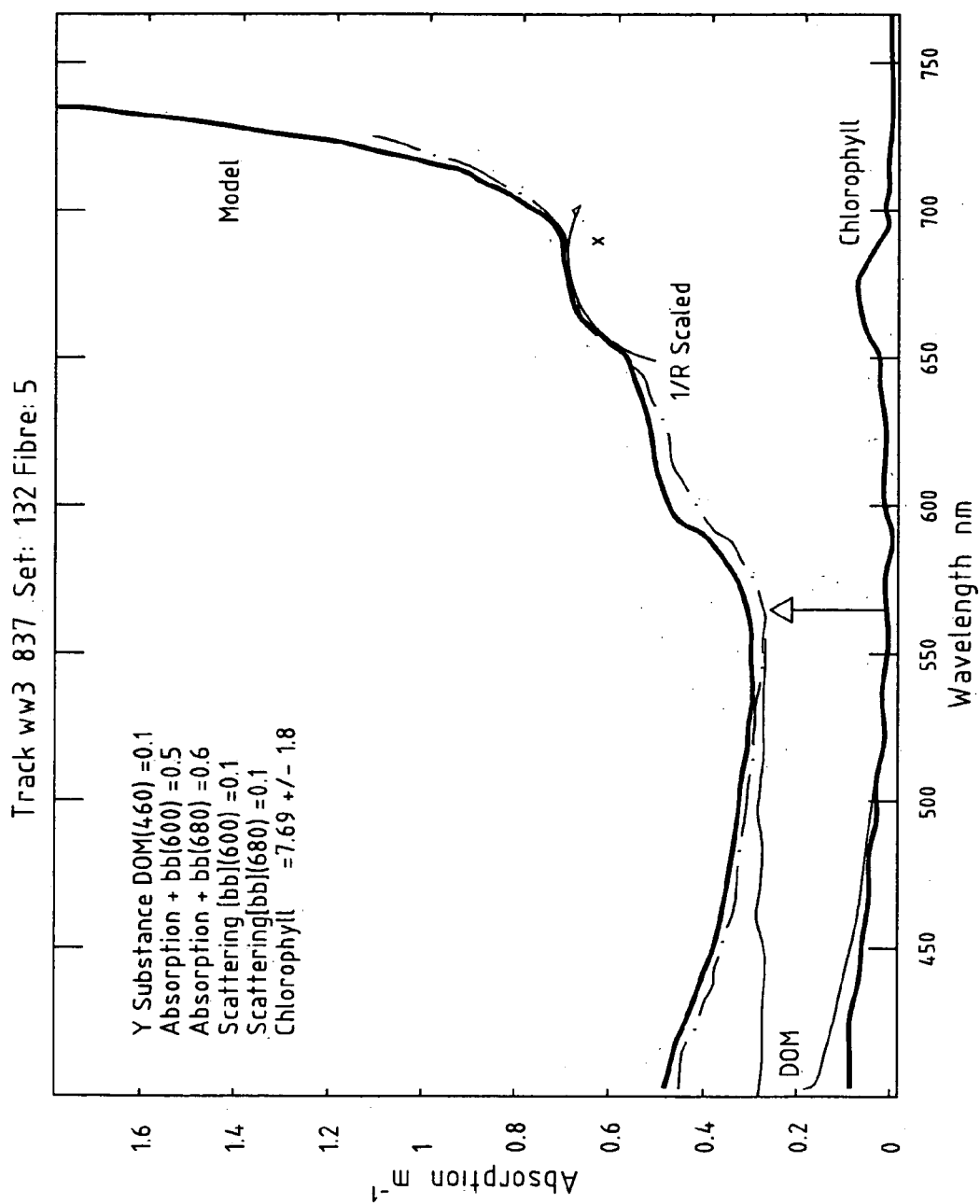
Figure 15:
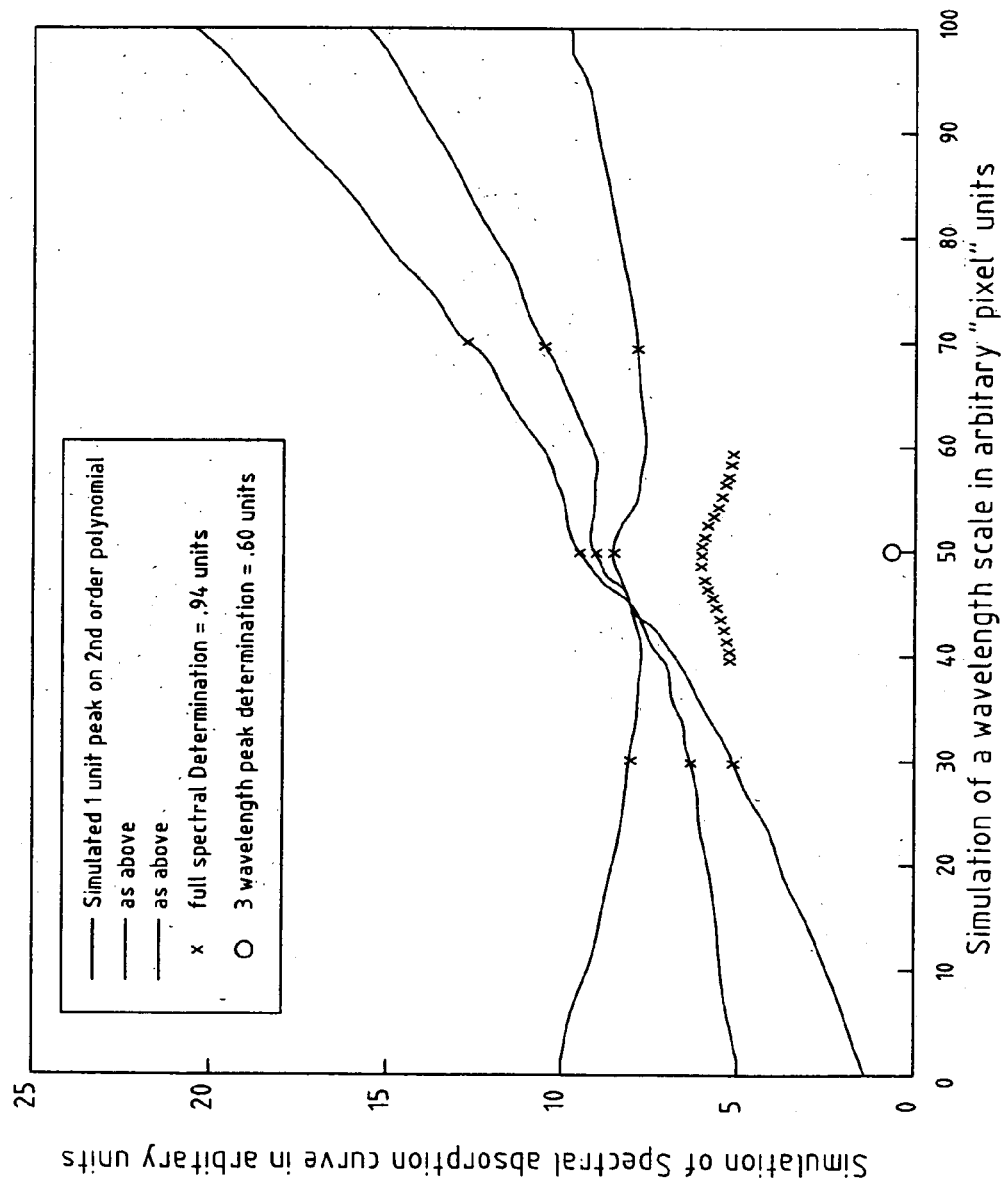

FIGS. 4 to 8 show how certain constituents may be detected from a body of water, FIG. 9 is a typical breakdown of absorption for one test carried out, FIG. 10 is a comparison of the reflection for high and low levels of chlorophyll, FIG. 11 demonstrates some of the absorption spectrum relevant to the invention, FIG. 12 is a comparison of pure water reflection with that of the Bay of Biscay, FIG. 13 is the reflectance of another body of water, FIG. 14 shows another absorption spectrum for a body of water, and FIG. 15 shows a comparison of various spectral analysis methods.

Figure 1:
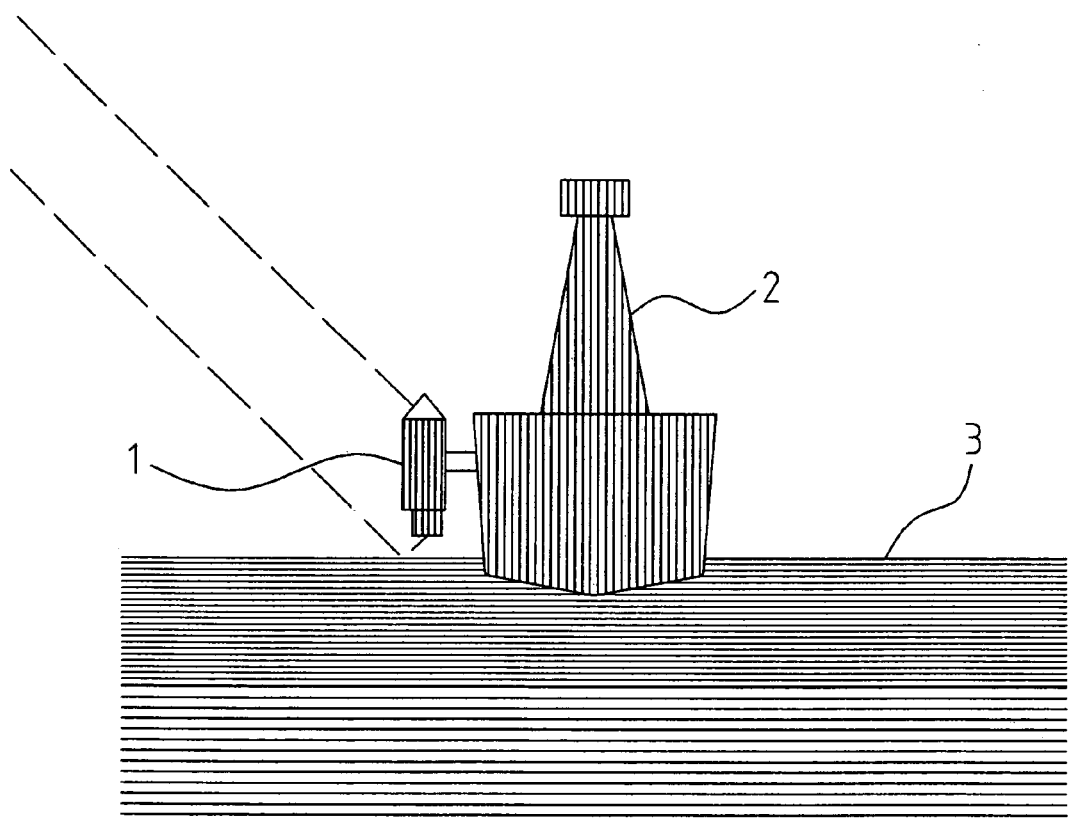
FIG. 1 is a view of a device according to the invention mounted on a buoy.

Referring to FIG. 1, there is illustrated a schematic of an apparatus of the invention in which a spectrometer 1 is mounted on a buoy 2 in the water 3. Other equipment could be also mounted on the buoy or alternatively the datum from the spectrometer could be transmitted to a master station via wireless or the like. However, this is of relatively little importance.

Figure 2:
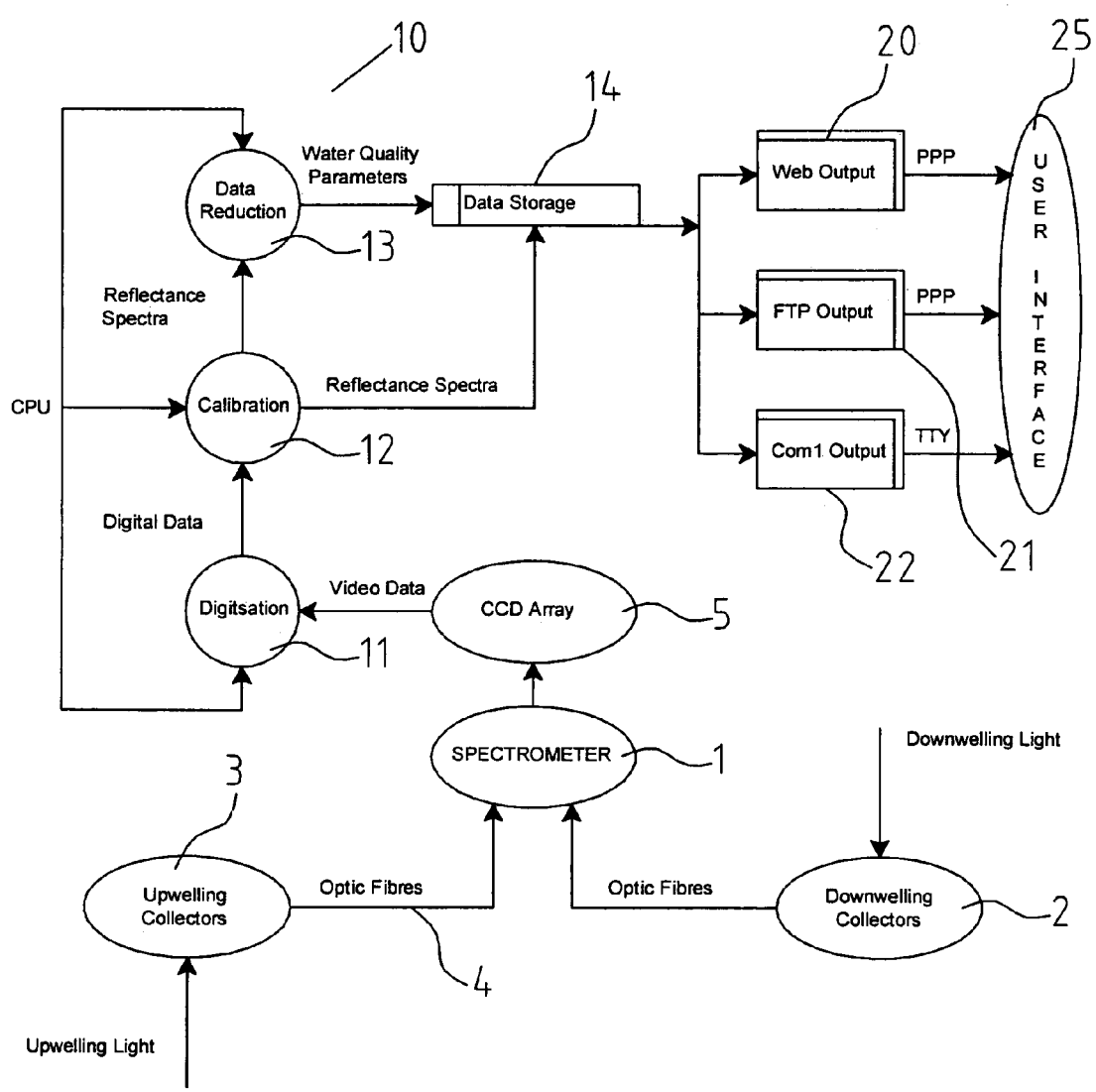
FIG. 2 is a schematic view of an embodiment of the invention.

Referring now to FIG. 2, there is illustrated the spectrometer 1 and its associated equipment in diagrammatic form which comprises a spectrometer 1 connected to a downwelling light collector 2 and an upwelling light collector 3, all of which deliver optic fibre inputs 4 to the spectrometer 1 which also includes a CCD monochrome camera 5. The CCD camera 5 feeds a central processing unit (CPU), indicated generally by the reference numeral 10, having a digitiser 11 for capture of the video data from the CCD camera 5 and includes calibration equipment 12, and data reduction equipment 13 and data storage 14. The calibration equipment 12 is to provide a calibration surface. The CPU 11 is programmed to acquire and integrate the light detected by the camera and to carry out the analysis and apply the algorithms which are described below. The data storage is shown connected to a web output 20, an FTP output 21 and a COM output 22, all of which can be accessed by a user interface 25. As explained below, the system is calibrated initially by replacing the target water surface with a white or grey target of known reflectance. Ideally, an additional internal reference reflectance surface is observed from time to time for system performance monitoring and correction under control of the CPU 11.

It will be appreciated that various aspects of the invention may be embodied on a computer that is running a program or program segments originating from a computer readable or usable medium, such medium including but not limited to magnetic storage media (e.g. ROMs, floppy disks, hard disks, etc.), optically readable media (e.g. CD-ROMs, DVDs, etc.) and carrier waves (e.g., transmissions over the internet). A functional program, code and code segments, used to implement the present invention can be derived by a skilled computer programmer from the description of the invention contained herein.

It will be appreciated therefore that a computerised program may be provided providing program instructions which, when loaded into a computer, will constitute the means for carrying out the methods in accordance with the invention and that this computer program may be embodied on a record medium, a computer memory, a read only memory or carried on an electrical carrier signal.

Figure 3:
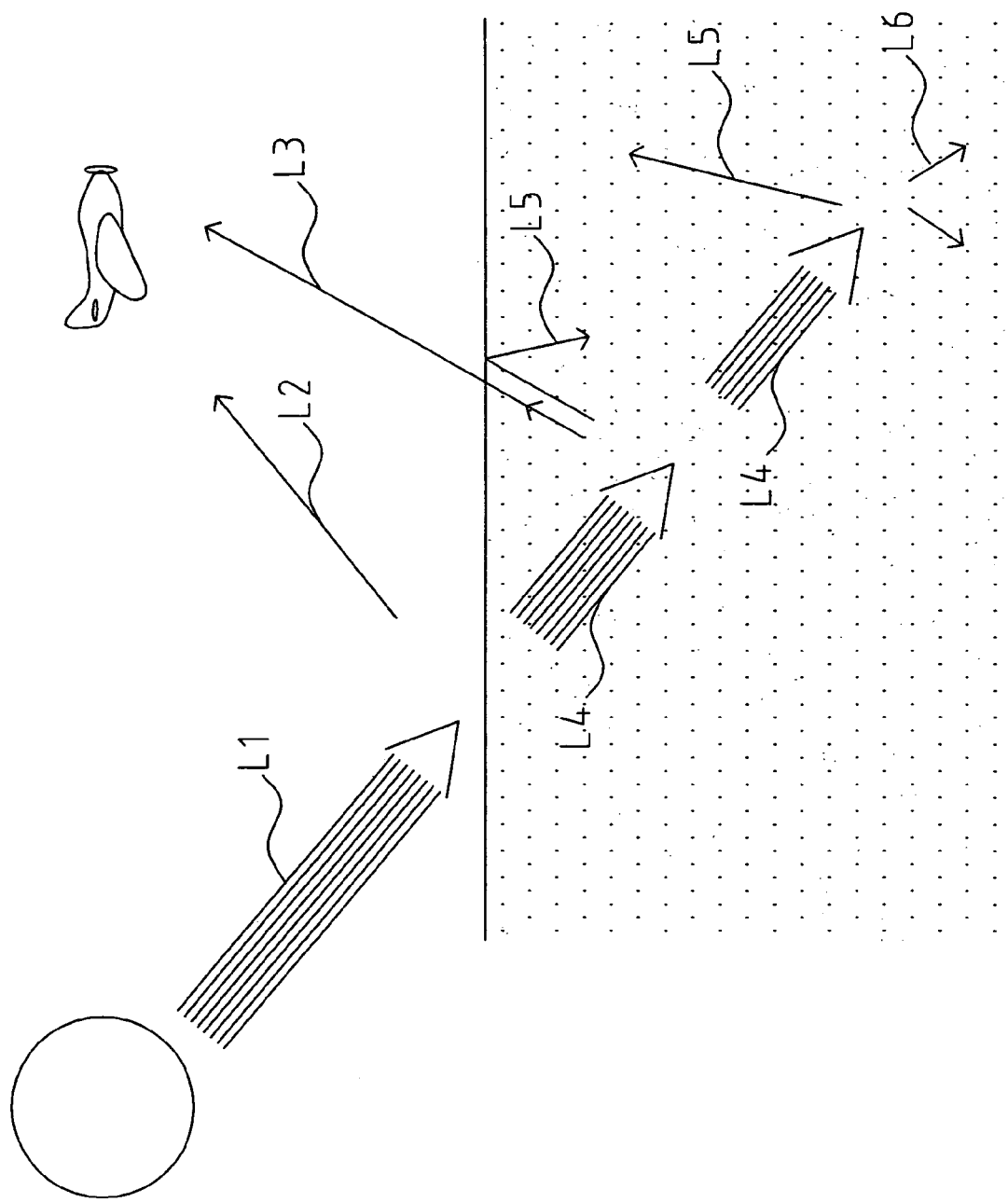
FIG. 3 is a view demonstrating how light is reflected from water.

FIG. 3 demonstrates how light reflected from water is affected by both the scattering and absorption properties of the water. Clear water containing minimal contaminants absorbs most of the light with very low reflectance in the range of less than 1%. The presence of contaminants in water results in the scattering of light resulting in reflectance. The back scattering of light is an indicator of particulate matter present in the water which scatters light. This is strongly correlated to the turbidity of the water. In FIG. 3, the light is identified by arrows as follows:

| L1 | downwelling sunlight |
| L2 | reflected surface upwelling light |
| L3 | reflected backscattered upwelling light |
| L4 | absorption |
| L5 | back scatter |
| L6 | forward scatter |

Certain substances absorb with unique features at particular wavelengths. For example yellow substance absorbs light in the blue region of the spectrum and this arises predominately from the presence of dissolved organic matter of all types. In coastal areas it is mostly indicative of fresh water plumes. The additional absorption in the water at 580 nm can arise in the presence of either chlorophylls related material or sedimentary matter. Sediments can be expected to have a greater back scatter to absorption ratio.

If the spectrum of reflected light is monitored, relative to the incident light, the spectral reflectance is measured. The pigment in chlorophyll, for example, has a distinct effect on this reflectance, absorbing light in the blue and red regions. Specific characteristic reference spectra can be calculated for different pigments and these in turn can be used to calculate the concentration of the pigment present in the water.

The present invention is thus based on the known relationship between the reflectance of any fluid and the absorption and scattering properties of that fluid. This relationship has been determined by radiative transfer calculations and can be found in the literature. In water reflectance is typically described by:

$$R(\lambda) = \frac{k \cdot b_b(\lambda)}{a(\lambda)}$$

or by some variation on this expression, such as:

$$R(\lambda) = \frac{k \cdot b_b(\lambda)}{a(\lambda) + b_b(\lambda)}$$

where $R(\lambda)$ is the spectral reflectance,
 $b_b(\lambda)$ is the back-scattering coefficient of all the water constituents, including water itself,
 $a(\lambda)$ is the absorption coefficients of all water constituents including water itself, and
 k is a constant dependent on the geometry of illumination.

The essential feature of these relationships is that reflectance is inversely proportional to absorption; and when absorption contains spectral features that are unique to it (i.e. not present in the backscattering coefficient), then the relative change in reflectance with wavelength will be directly proportional to the negative of the relative change in absorption with wavelength.

In applying such a relationship to above water reflectance a typical working version of the relationship might be as below. This can take into account the relative importance of scattering, the absorption of key constituents, and surface reflectance. Over a limited spectral range, the spectral variations of some constituents may dominate in determining the spectral variation of reflectance. In some regions the spectral variations of water dominate. In others that due to Chlorophyll, or dissolved organic matter may dominate. In the spectral region above about 550 nm (550 nm to 760 nm for example), a working version of the relationship between above water reflectance and absorption and scattering, valid over limited spectral ranges, would be:

$$R(\lambda) - R_o = \frac{k b_b}{(a_w(\lambda) + \chi \cdot a^*_{chl}(\lambda) + a_o)} \quad \text{Equation 1}$$

where $R(\lambda)$ is the measured spectral reflectance, $R_o$ is an additional component of reflectance, possibly from the surface, from foam (white-caps) or specular glint, without notable spectral features.

$b_b$ is the back-scattering, assumed to be without notable spectral features. (In practice, $b_b$ might often be represented by a linear spectral function $b_b(\lambda) = b_o + b_1 \lambda$, or by a slowly varying exponential spectral function)

$a_w(\lambda)$ is the known spectral dependence of water absorption, particularly featured at 580 to 620 nm and above 650 nm.

$a_{chl}^*(\lambda)$ is the known specific spectral absorption coefficient of chlorophyll, particularly featured around 675 nm, and $\chi$ the concentration of chlorophyll.

$a_o$ is an additional component of [absorption+back-scattering] considered not spectrally featured over the restricted wavelength region, generally referred to hereinafter as absorption.

In the blue part of the spectrum (below 500 nm) the absorption effects of water do not dominate. Here the effects of dissolved organic matter can be significant or even dominate and the term $a_w$ can be replaced by a term $a_{ys}(\lambda)$ representing the absorption of dissolved organic matter (DOM). [Sometimes referred to as Yellow substance (YS)].

A spectral feature of water or any of its constituents is notable or significant if the first derivative of this spectral absorption feature with respect to wavelength, and/or its variation with wavelength dominates over the first derivative of the absorption spectrum of all other constituents.

Presuming it is desired to, for example, measure a particular constituent in a body of water, the steps would be carried out of:

1. Measure the reflectance of the body of water.
2. Choose the constituent you want to measure and note significant wavelength range for that constituent.
3. The datum spectrum for water is prepared.
4. Remove the additional reflectance which is not considered spectrally featured over the chosen wavelength region.
5. Use the best formula available to convert reflectance to absorption in the wavelength region chosen. This formula will convert the reflection to absorption in the sense that the spectral curve will be of the correct shape but it will not have any units of measurement.
6. This inverse reflectance curve is then matched to the absorption curve of water within that region which converts this inverse reflectance curve to an absorption curve with units of absorption. Effectively the match entails manipulating the unitless spectrum until it matches the spectral features of water where these dominate thus fit the shape and when the shapes within the range match, you have scaling and offset. Then the spectrum for water is subtracted. A spectrum without units for the constituent being examined is prepared. It is then matched to the spectrum which is the spectrum less water.
7. The constituent in real units of absorption is extracted and the required constituent is then available. This can be iteratively repeated to find other constituents.

The order in which the constituents are chosen is arbitrary.

Specific pigments of interest could be carrotenoids, phycocyanins or industrial dyes such as effluent from factories.

Referring now to FIGS. 4 to 8, it is illustrated how chlorophyll, DOM and finally suspended matter and other pigments may be detected from a body of water.

Figure 4:
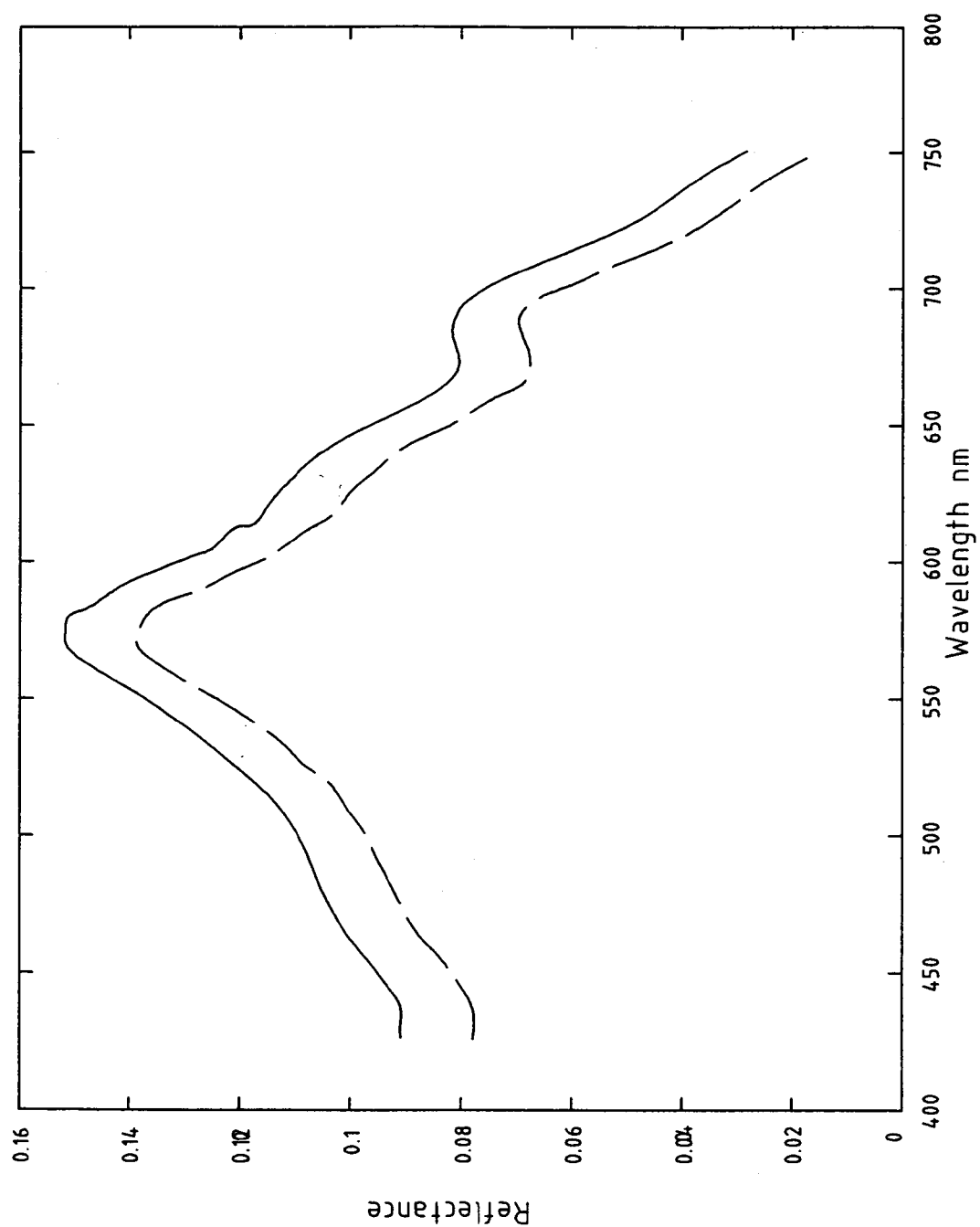
Figure 5:
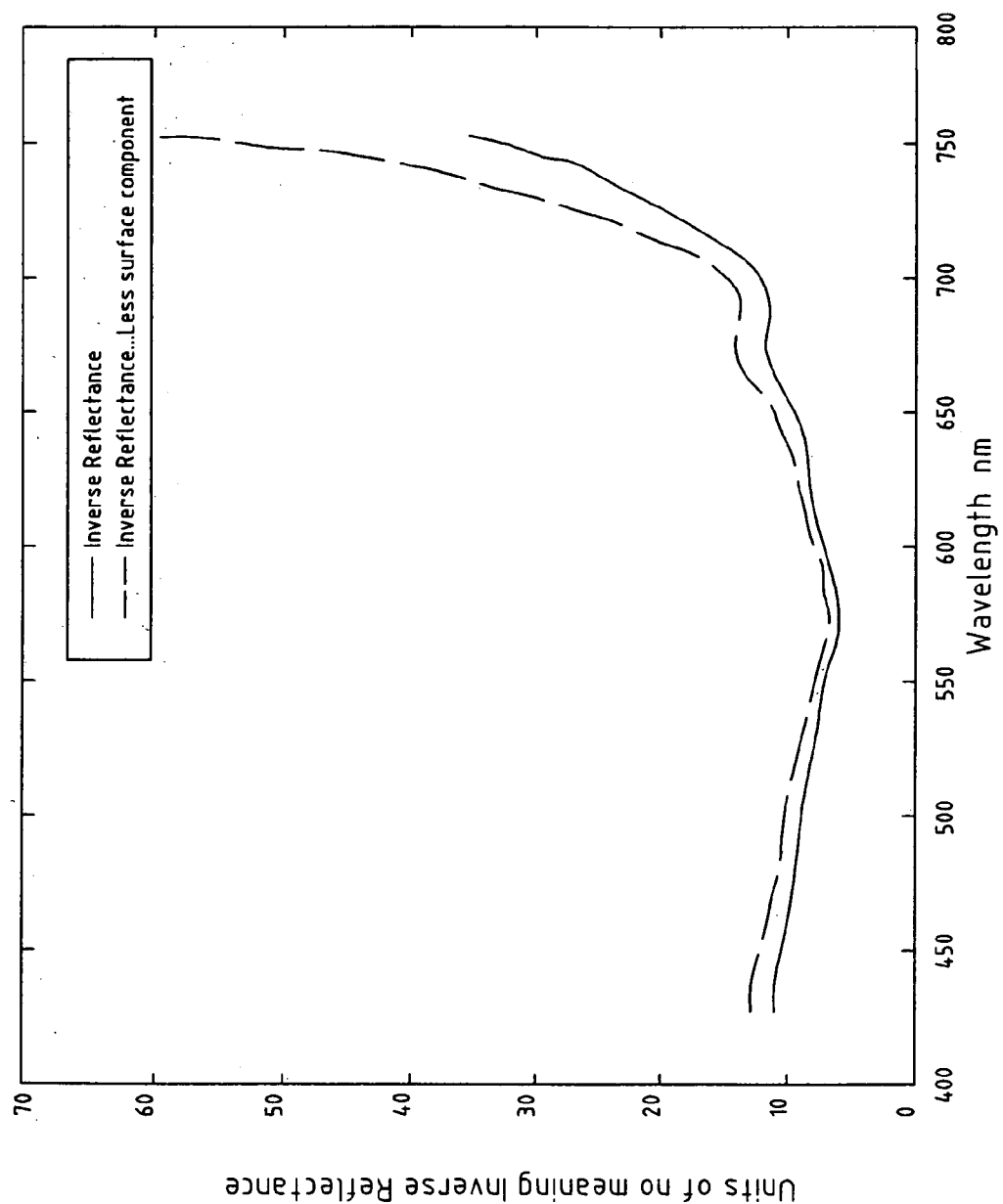

FIG. 4 shows the spectral reflectance measured from a body of water shown by the bold line, while the Interrupted line shows additional components of surface reflectance removed. FIG. 5 shows the inverse reflectance in units having no meaning, namely, by the full line showing $1/R(\lambda)$, while the interrupted line shows $1/[R\lambda - R_o]$.

Figure 6:
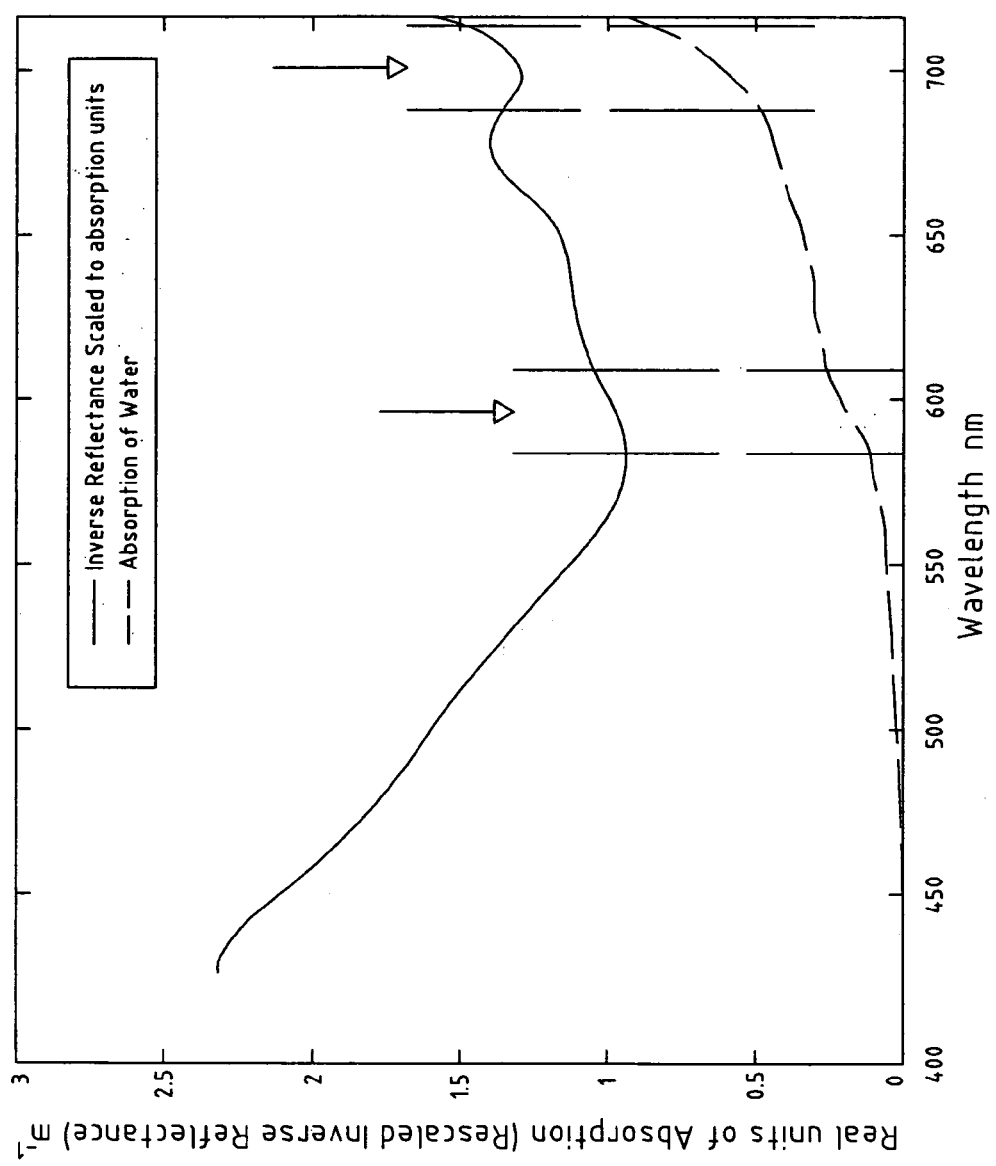

Referring now to FIG. 6, because chlorophyll is the chosen constituent being detected, the regions of the spectrum where the spectral absorption features of water dominate over those of the other constituents is chosen. For example, when chlorophyll is present, the-spectral region from 580 to 620 nm and above 690 nm are chosen for matching. Therefore, $1/[R(\lambda) - R_o]$ is rescaled by using the absorption spectrum for water which is shown by the interrupted lines. We now have absorption in real units. Thus:

$$\frac{1}{R} \propto a_{total}$$

$$\frac{1}{R} \propto a_w + \chi \, a^*_{chl} \lambda + a_{dom} + a_{sm+o}$$

where $a_w$=water absorption $a^*_{chl}$=specific chlorophyll absorption $\chi$=number of units of chlorophyll $a_{dom}$=dissolved organic matter absorption $a_{sm+o}$=suspended matter and other constituent absorption FIG. 6 shows the absorption spectrum as derived from the spectrum of FIG. 5 after it has been analysed in accordance with equation 1. A surface reflectance component $R_o$ of 3% has been subtracted. The regions of comparison are illustrated by arrows and the absorption of water is given by the interrupted line.

FIG. 7 now illustrates in full lines the spectrum for total absorption less water absorption and when the spectrum for chlorophyll is matched, the true spectrum for the chlorophyll is produced and subtracted so that now the interrupted lines show the spectrum for water with the chlorophyll subtracted. The amount of chlorophyll is also shown.

In FIG. 8, the full line now shows total remaining absorption, namely, of $$a_{total} - a_w - \chi a^*_{chl}(\lambda)$$

Then a typical spectrum for dissolved organic matter is plotted and extracted, as can be seen from FIG. 8, the final spectrum given by the interrupted lines is for suspended matter and other constituents.

FIG. 9 is a typical breakdown of an absorption for tests carried out in Dublin Bay in September 2000. The components of chlorophyll, DOM and additional absorption $a_o$ have been rescaled due to suspended matter which matched the data have been calculated. The components of the chlorophyll and DOM absorption are also shown separately at the lower part of the figure.

In the regions of notable water absorption features, the proportionality constant can be calculated by fitting a first order polynomial.

$$\frac{1}{R(\lambda)} = m \cdot a_w(\lambda) + c$$

$a_w$=known spectrum for water absorption in the region chosen wherein the residual absorption (and backscatter) due to water constituents is given by the offset c/m, and the desired proportionality constant which converts $$\frac{1}{R(\lambda)}$$

from arbitrary units into units of absorption (physical units: $m^{-1}$) is given by m. The quantity m found in this way represents the factors $kb_b$.

In another embodiment of the invention the inverse reflectance curve is matched to the absorption curve of water using a differentials method. The relative differential of R with respect to wavelength is related to the relative differential of $a_w$ with respect to the wavelength over the regions of notable water features:

$$\frac{\Delta R(\lambda)}{R(\lambda)} = -\frac{\Delta a_w(\lambda)}{a_{total}}$$

where $a_{total}$ is the sum of all absorption effects, including water. $R(\lambda)$, and $\Delta R(\lambda)$ are measured, $\Delta a_w(\lambda)$ is known, so that $a_{total}$ can be calculated.

We have found after extensive studies of the method to determine the scaling in absorption units of the inverse reflectance curve, that there are certain factors that affect the measurements. The studies are thus carried out based on the premise that normally, there are no non-linear spectral features in the chosen spectral regions suggested above, other than that due to water, in other words, in the chosen regions the spectral absorption features of water dominate.

In another embodiment of the invention, the effect of chlorophyll is derived directly from the reflectance in the region around 675 nm
using both:
(a) the known spectral absorption coefficient of water $a_w(\lambda)$ and
(b) the known specific spectral absorption coefficient of chlorophyll $a^*_{chl}(\lambda)$.

In this embodiment, the proportionality constant representing $kb_b$ is allowed to have a linear variation with wavelength, and the quantities $R_{o, \chi}$, and $a_o$ are adjusted (in that order) to achieve best fit.

In the above embodiment of the invention the estimate of the concentration of chlorophyll is measured in the range around 675 nm This estimate is then derived by a method which does not depend for its accuracy on the quality of other estimates; in particular the estimate of scaling factor from near 600 nm is not utilised.

In another embodiment of the invention, the effect of suspended matter is derived directly from portions of the reflectance in the regions from 580 to over 750 nm using:
(a) the known absorption of water $a_w(\lambda)$ alone In this embodiment, the proportionality constant representing $kb_b$ is allowed to have a linear variation with wavelength, and the quantities $R_o$ and $a_o$ are adjusted (in that order) to achieve best fit.

In the above embodiment of the invention for the estimate of optical effects of suspended matter the measure is made independent of any chlorophyll present if the measurement is conducted in the spectral range above the significant chlorophyll absorption region, viz above 700 nm. This estimate is then derived by a method which does not depend for its accuracy on the quality of other estimates, and yields information on suspended matter concentration expressed in physical units ($m^{-1}$).

In a preferred embodiment of the invention an estimate of the back scattering coefficient ($b_b$) is measured at the regions of significant water absorption features, notably near 600 nm and near or above 675 nm (depending on likely presence or absence of chlorophyll). If values of k from the literature are used [k=0.3 for the sun at the zenith, and dependent on the cosine of the solar zenith angle] an estimate of $b_b$ is obtained .(in $m^{-1}$). This is an aspect of the invention which requires that reflectance be itself determined with absolute accuracy. For all other methods described methods described reflectance can be determined in arbitrary units. This estimate of $b_b$ is directly comparable with the measurement of scattered light made by some turbidity meters.

In a preferred embodiment of the invention, all the optical information derived about the suspended mater can be used to allow different classes of suspended matter to be identified. Unlike turbidity (one factor describing the suspended matter), this embodiment provides a multi-parameter description of the suspended mater a number of estimates of [absorption+scattering] at different wavelengths, together with an equivalent number of estimates of backscattering are provided.

In a preferred embodiment of the invention the estimate of yellow substance or dissolved organic matter are measured in the blue range a(440)–a(580) nm (in $m^{-1}$).

When the proportionality factor(s) for converting $$\frac{1}{R(\lambda)}$$

into units of absorption is(are) extended to wider spectral regions an estimate of "residual absorption" is obtained by subtracting the spectral absorption of water $a_w(\lambda)$. The residual absorption shows notable spectral features of all water constituents. In particular the spectral absorption features of chlorophyll-a at 675 nm, of dissolved organic matter in the blue and other natural pigments such as chlorophyll-b, chlorophyll-c, phycocyanin, carotenoids, are of most interest. The absorption effects of suspended matter in general, even if not endowed with spectral features will also be quantified by this residual absorption, which may include backscatter.

In one method according to the invention, the steps are performed of:

measuring down-dwelling light $S_{d1}$ and up-dwelling light $S_{u1}$ from a reference surface at time $t_1$; and measuring down-welling light $S_{dt}$ and up-dwelling light $S_{ut}$ from a target surface at time t.

Then the reflectance of the target $R_t$ as a fraction of the reference surface reflectance is then given by:

$$R_t = \frac{S_{ut}}{S_{u1}} \frac{S_{d1}}{S_{dt}}$$

It is known from radiative transfer calculations that for reflectance of water (Equation I above):

R is proportional to $b_b/a$ for moderate content of scattering where $b_b$=the back scattering coefficient and a is the total absorption coefficient for water 1/R is proportional to a $b_b$ only varies slightly with wavelength by comparison with a, and there is a need to find out the proportionality between 1/R and a.

The inverse reflectance 1/R is compared with the known absorption spectrum of water.

If necessary, determine additional reflectance from the surface $R_o$, which can be recognised by the absence of spectral features associated with the spectral absorption to water. In this case $R(\lambda)=R_t-R_o$ It is necessary to use one or more of the known absorption features of water to find the proportionality and to avoid any features too close to other pigment effects, such as the known chlorophyll feature at 675 nm. For example the feature at 580–610 nm is appropriate although knowledge of the absorption curve of natural waters in the 690–740 region is a good alternative.

The principal feature of the invention is that the known absorption features of water provide an absolute calibration factor or factors for the conversion of inverse reflectance into absorption. Refinements in the methods of determining these factors can be expected with the application of additional well known curve-fitting routines, other than those outlined in this specification.

FIG. 10 compares the reflectance of the sea water determined when high levels of chlorophyll are present in the water with the reflectance for low chlorophyll concentration.

It must be noted that the particular wavelengths that are to be considered to calculate DOM, chlorophyll and accessory pigment concentrations is dependent on the type of waters studied. For example, some of the waters around Ireland, Great Britain and Northern Europe can be described as eutrophic waters and in this area chlorophyll absorbs light in the red region, absorbing maximally at 675 nm and DOM dominates in the blue region. However, in the beautiful clear blue oligotrophic waters of the Americas, the chlorophyll absorption in the blue region, circa 440 nm can dominate this spectral region. The exact same techniques will only apply in this region if the factor(s) relating inverse reflectance to absorption can be extrapolated with accuracy from the 600 and 700 nm regions back to the blue region around 440 nm. In certain circumstances this may be possible. This would have the advantage of allowing chlorophyll concentration to be determined at greater depths, as the concentration is determined over a depth of approximately $$\frac{1}{a_{total}} m^{-1}$$

This test was carried out in Dublin Bay in September 2000. The effect of chlorophyll in increasing reflectance through increasing back scatter and reducing inflection at the absorption maximum of chlorophyll at 675 nm can be noted.

FIG. 11 demonstrates some of the absorption spectra that are relevant to this application. The absorption spectrum of pure water $a_w(\lambda)$ showing particular features at 580 nm and continuing past a peak at 740 nm is shown. This is well documented in the literature. Also shown are the spectra for chlorophyll (100 times $a_{chl}*(\lambda)$) and the absorption spectrum for DOM. This produces an amount of DOM producing an effective absorption of $0.7_{m-1}$ at 440 nm.

It is possible to determine the concentration of contaminants in water by comparing the reflectance of water to the known absorption of clear water using the following assumptions:

That in general reflectance is inversely proportional to absorption $$R \propto b_b/a \text{ or}$$

$$1/R \propto a/b_b$$

where R is reflectance, $b_{bb}$ is back scatter and a is absorption.

(It must be noted that in the literature it has been also suggested that $$R \propto b_b/(a+b_b))$$

Both these expressions are consistent with Equation I above which is used as the basis for explaining the operation of the invention.

If reflectance is measured over short wavelength regions of the spectrum, absorption fluctuates, whilst back scatter remains comparatively constant.

Therefore in some regions $1/R(\lambda) \propto (a_w(\lambda)+$relatively constant components of absorption and backscattering)

1/R curves can be superimposed onto the absorbance curve for pure water using algorithms and the contribution of the contaminants present to the total absorption can be calculated.

For comparative purposes FIG. 12 demonstrates pure water reflectance compared to a particular chosen reflectance of the Bay of Biscay. In order to "match" the curves, the pure water reflectance shown by interrupted lines was simulated by adding a grey or spectrally flat constituent (equivalent to $a_o$ in Equation I or to the "relatively constant components referred to above). For this figure the flat absorption component had an absorption coefficient of 0.54 $m^{-1}$.

FIG. 13 illustrates the reflectance of water using a prototype version of the present invention. The reflectance of a water body has been measured and the absorption has been utilised to rescale the 1/R curve. The absorption effect of water has been subtracted resulting in residual absorption. FIG. 14 shows the effect of DOM in the blue and chlorophyll.a at 675 nm. An algorithm was used to determine the chlorophyll value and the fitted chlorophyll peak is illustrated by the arrow A.

In the past chlorophyll concentrations have been estimated by measuring absorption at a finite number of wavelengths (two, or occasionally 3). FIG. 15 illustrates, for this particular scenario, that full spectral (or hyperspectral) methods are superior to techniques using a small number of fixed bands for determination of the height of a spectral feature. For this illustration a gaussian pigment feature of height one unit is simulated and added to a second order polynomial spectral simulation. The height of the feature is estimated from the band points at 30, 50 and 70 using height(50)−[height(30)+height(70)/2]

An estimate of 0.60 is obtained. Using full spectral techniques and curve fitting routines on the region around 50, the height is more correctly estimated at 0.94, nearer to 1. The finite number of bands technique works well for pigment peaks superimposed on purely linear spectral variations. However, when the spectral variations are non-linear, or where one of the bands are affected by other pigment effects then the hyperspectral method is superior in estimating the true height of a pigment peak. In fact, in this scenario the finite band method often yields incorrect results.

Some algorithms for converting the data in order to superimpose the 1/R curve onto the pure water absorption curve are disclosed, although the invention is not limited to these methods and it is expected that other methods can be devised.

In summary, the methods disclosed are
1. Proportionality constant
2. Differentials method
3. Radiative transfer calculations (RTC)
1. Proportionality constant is calculated by fitting a first order polynomial in the region 580–610 nm. Then $1/R = m.a_w + c$ where $a_w$ is the known spectrum for water absorption.
2. Differential methods of determining this scaling proportionality factor are as follows: a differential is made of R with respect to the wavelength equal to the differential of $a_w$ with respect to the wavelength.

$K(1/R_{580} - 1/R_{610}) = a_{w580} - a_{w610}$ where K= is the equivalent of m in the previous expression.
3. RTC reflectance algorithms was developed for lake monitoring as published. The chlorophyll concentration is adjusted using linear least squares until:

$R\_(a_w + \chi a^* \text{chlorophyll}) = a + \lambda$ where $_\chi a^*$chlorophyll=the calculated concentration of chlorophyll and a* is the known specific absorption of chlorophyll in the 600 to 700 nm region.

While in the embodiments described above, there has been a definite progression from chlorophyll measurement to DOM measurement and to the measurement of other residual matter, there is no need to carry it out in this order. It is envisaged, for example, that if it was decided that DOM was the most important thing to be analysed, possibly different spectra matching techniques would be used more suitable to obtain a more accurate measure of DOM.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail within the scope of the claims.

The invention claimed is:

1. A spectrographic analysis method of determining the presence of a chosen constituent in water where such constituent gives rise to optically identifiable distinct characteristics comprising the steps, not necessarily sequentially, of:
   preparing an absorption spectrum of clear water as a datum spectrum;
   preparing a full spectrum measurement of the reflectance of the body of water;
   deriving a potential absorption spectrum of the body of water from the reflectance measurement as a sample spectrum;
   matching the sample spectrum to the datum spectrum at wavelength regions of the spectrum where water absorption dominates;
   estimating a proportionality factor between the potential absorption spectrum and the datum spectrum during matching;
   estimating the total measured absorption using the proportionality factor;
   choosing a wavelength range over which the chosen constituent has optically identifiable distinct characteristics;
   using the difference between the two absorption spectra to obtain a measure of the amount of the constituent present.

2. The spectrographic analysis method as claimed in claim 1 where the required optical characteristic is present in the absorption spectrum and the method comprises the steps of:
   matching the sample spectrum to the datum spectrum at wavelength regions of the spectrum where the datum spectrum is the dominant contributor to spectral change to give a measure of the total absorption of the sample water;
   taking a known spectral signature of the chosen constituent;
   removing the datum spectrum from the sample spectrum to leave a residual spectrum for all the constituents in the water;
   matching a spectral signature for a prime chosen constituent to the residual spectrum at a wavelength region where the chosen constituent is dominant; and
   abstracting the matched spectrum as a measure of the amount of the prime chosen constituent in the water.

3. The method as claimed in claim 2, in which the wavelength regions chosen for matching with the datum spectrum are those closest to where the chosen constituent is dominant.

4. The method as claimed in claim 2, in which the matched spectrum is removed from the residual spectrum to give a new residual spectrum.

5. The method as claimed in claim 4, in which a spectrum signature of another chosen constituent is matched to the new residual spectrum abstracted and removed as for the prime constituent.

6. The method as claimed in claim 2, in which the constituents chosen are chlorophyll as the prime constituent, then DOM and the new residual spectrum, after the spectra for chlorophyll and DOM has been removed, is used as a measure of suspended matter and other constituents.

7. The method as claimed in claim 2, in which additionally the spectrum attributable to surface reflection is identified and removed from the full spectrum measurement of the reflectance of the body of water prior to devising the potential absorption spectrum.

8. The method as claimed in claim 2, in which when in the chosen region where the datum spectrum is dominant there is also a spectrum relating to another constituent which could affect the estimate of the constituent being measured, the spectrum of this other constituent is first obtained and combined with the datum spectrum to provide a modified datum spectrum for removal from the sample spectrum.

9. The method as claimed in claim 1, in which:
the total spectrum of reflectance is taken;
a region of significant water absorption is chosen;
the effect of the geometry of the illumination is determined and the backscattering is estimated.

10. Apparatus for carrying out the method as claimed in claim 1 comprising:
means for collecting light reflected from a body of water;
a spectrometer for preparing a reflectance spectrum of the reflected light; and
a processor unit having processing means to carry out the steps of the method using the reflectance spectrum.

11. A computer program comprising program instructions for causing a computer to carry out the steps of the method of claim 1.

12. A computer program comprising program instructions when loaded into a computer constitute the processing means as claimed in claim 10.

13. The computer program as claimed in claim 11 embodied on a record medium.

14. The computer program as claimed in claim 11 stored in a computer memory.

15. The computer program as claimed in claim 11 embodied in a read only memory.

16. The computer program as claimed in claim 11 carried in an electrical signal earner.

17. The method as claimed in claim 1, wherein the method further comprises the step of:
estimating a back scattering coefficient ($kb_b$) of the body of water and allowing $kb_b$ to have a linear variation with the wavelength to achieve best fit during matching.

18. A spectrographic analysis method of determining the presence of a chosen constituent in water where such constituent gives rise to optically identifiable distinct characteristics comprising the steps, not necessarily sequentially, of:
preparing an absorption spectrum of clear water as a datum spectrum;
preparing a full spectrum measurement of the reflectance of the body of water,
deriving a potential absorption spectrum of the body of water from the reflectance measurement as a sample spectrum;
matching the sample spectrum to the datum spectrum at wavelength regions of the spectrum where water absorption dominates;
estimating a proportionality constant between the potential absorption spectrum and the datum spectrum during matching;
estimating the total measured absorption using the proportionality constant;
choosing a wavelength range over which the chosen constituent has optically identifiable distinct characteristics; and
using the difference between the two absorption spectra to obtain a measure of the amount of the constituent present.

19. The method as claimed in claim 18, wherein the proportionality factor is a proportionality constant and the method further comprises the step of:
estimating a back scattering coefficient ($kb_b$) of the body of water and allowing $kb_b$ to have a linear variation with the wavelength to achieve best fit during matching.

* * * * *